United States Patent
Lee et al.

(10) Patent No.: US 7,373,600 B2
(45) Date of Patent: *May 13, 2008

(54) DICOM TO XML GENERATOR

(75) Inventors: Kwok Pun Lee, Flushing, NY (US); Jingkun Hu, Nyack, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 650 days.

This patent is subject to a terminal disclaimer.

(21) Appl. No.: 09/818,715

(22) Filed: Mar. 27, 2001

(65) Prior Publication Data

US 2002/0143824 A1    Oct. 3, 2002

(51) Int. Cl.
G06F 15/00  (2006.01)

(52) U.S. Cl. .................... 715/523; 715/513; 715/530

(58) Field of Classification Search ............. 715/513, 715/523, 530; 707/1, 102, 2–3
See application file for complete search history.

(56) References Cited

U.S. PATENT DOCUMENTS

| | | | | |
|---|---|---|---|---|
| 5,708,828 | A | | 1/1998 | Coleman .................... 395/785 |
| 6,101,407 | A | * | 8/2000 | Groezinger ................. 600/407 |
| 6,151,608 | A | | 11/2000 | Abrams ...................... 707/204 |
| 6,182,029 | B1 | * | 1/2001 | Friedman .................... 704/9 |
| 6,507,857 | B1 | * | 1/2003 | Yalcinalp ................... 715/513 |
| 6,668,354 | B1 | * | 12/2003 | Chen et al. ................. 715/517 |
| 6,725,231 | B2 | | 4/2004 | Hu et al. ....................... 707/1 |
| 6,732,330 | B1 | * | 5/2004 | Claussen et al. ............ 715/513 |
| 7,024,413 | B2 | * | 4/2006 | Binding et al. ............. 707/101 |
| 2001/0037346 | A1 | * | 11/2001 | Johnson ...................... 707/513 |
| 2002/0049790 | A1 | * | 4/2002 | Ricker et al. ............... 707/513 |
| 2002/0052899 | A1 | * | 5/2002 | Fujikawa .................... 707/530 |
| 2002/0087571 | A1 | * | 7/2002 | Stapel et al. ................ 707/100 |
| 2002/0087971 | A1 | * | 7/2002 | Cochran et al. ............... 725/31 |
| 2002/0111932 | A1 | * | 8/2002 | Roberge et al. ................ 707/1 |
| 2002/0122057 | A1 | * | 9/2002 | Maloney ..................... 345/744 |

FOREIGN PATENT DOCUMENTS

| | | |
|---|---|---|
| EP | 0848554 | 6/1998 |
| WO | WO9748230 | 12/1997 |

(Continued)

OTHER PUBLICATIONS

Clunie, "DICOM SR Meets XML -beyond the hype", published Mar. 29-30, 2000, http://medical.nema.org/dicom/srworkshop/srxml20000330.ppt.*

(Continued)

Primary Examiner—Thu Huynh

(57) ABSTRACT

A conversion system converts DICOM SR information from a DICOM-formatted file into an XML representation. By providing a mapping between DICOM SR and XML, the DICOM SR content material can be more easily processed by application programs that are DICOM-specific, such as medical analysis programs, as well as by application programs that are not DICOM-specific, such as routine clerical or data-management programs. In a preferred embodiment, a two-phase conversion is employed. The DICOM information is parsed and Fig converted directly into a "raw" XML data set. Thereafter, the "raw" XML is transformed into a proper XML output form, via an XSLT processor. Changes to the desired XML output form can thus be effected via changes in the corresponding XSLT stylesheets.

10 Claims, 4 Drawing Sheets

FOREIGN PATENT DOCUMENTS

WO     WO9818091     4/1998
WO     WO9918722     4/1999

OTHER PUBLICATIONS

Clunie, "SR Object Model (SR-OM)—Towards an API for toolkits", published Mar. 29-30, 2000, http://medical.nema.org/dicom/srworkshop/srapi20000330.ppt.*

Clunie, "Structure Reporting—More Complex Examples", published Mar. 29-30, 2003, http://medical.nema.org/dicom/srworkshop/srcx20000330.ppt.*

Clunie, "DICOM SR Tools -dicom3tools", published Mar. 29-30, 2000, http://medical.nema.org/dicom/srworkshop/srdct20000330.ppt.*

DICOM Standards Committee, Digital Image and Communications in Medicine (DICOM), version Mar. 2000.*

Oosterwijk, "DICOM explained in the context of Structured Reporting", Mar. 29-30, 2000.*

Clunie (herein after Clunie1), "DICOM Structured Reporting", copyright 2000, pp. 7-13, 31, 237, 306-314, 325-344.*

Torii et al., "The inforamation management system based on XML bidirectional transfomration technology", pp. 341-348, issued Mar. 2002.*

Xu et al., "Using XML in a generic model of mediators", May 1999, pp. 1-14.☐☐Shobowale, "SGML, XML and the Document-Centered Approach to Electronic Medical Records", ASIS Bullentin, Nov. 1998, page.*

Shobowale, "SGML, XML and the Document-Centered Approach to Electronic Medical Records", ASIS Bullentin, Nov. 1998, pp. 1-7.*

Wang et al., "Potential Use of Extentible Markup Language for Radiology Reporting: A Tutorial", RSNA copyright 2000, pp. 1-11.*

David Clunie, "DICOM SR Implementation" from "DICOM Structured Reporting: Implementation Experience (NEMA SR Implementers Workshop 2001)", which is http://www.dclunie.com/papers/sr20010608_dac.pdf, pp. 1-38.*

*Supplement 23: Structured Reporting Storage SOP Classes* to the DICOM Standard, published by the DICOM Standards Committee, 1300 N. 17th Street, Rosslyn, VA 22209 USA, Apr. 6, 2000.

U.S. Appl. No. 09/686,401, filed Oct. 10, 2000, Tirado-Ramos et al.

\* cited by examiner

```
<xsl:include href="Patient_IE.xsl"/>
<xsl:include href="Study_IE.xsl"/>
<xsl:include href="Series_IE.xsl"/>  ~412
<xsl:include href="Equipment_IE.xsl"/>
<xsl:include href="Document_IE.xsl"/>
<!--template for top-level element-->
<xsl:template match="report">  ~414                            416
  <SRDocument>
    <xsl:attribute name="report_id"><xsl:value-of select="@id"/>
    <xsl:attribute name="report_date"><xsl:value-of select="@date"/>
    <xsl:call-template name="Patient_IE"/>
    <xsl:call-template name="Study_IE"/>
    <xsl:call-template name="Series_IE"/>   ~418
    <xsl:call-template name="Equipment_IE"/>
    <xsl:call-template name="Document_IE"/>
  </SRDocument>
</xsl:template>
```

```
<xsl:template name="Patient_IE">
  <Patients>
    <Patient>
422 —<xsl:call-template name="patients_name_template"/>
424 —<xsl:call-template name="patient_id_template"/>
426 —<xsl:call-template name="patients_birth_date_template"/>
      <xsl:call-template name="patients_sex_template"/>
      <xsl:apply-templates select="patients_birth_time"/>
      <xsl:apply-templates select="other_patient_ids"/>
      <xsl:apply-templates select="other_patient_names"/>
      <xsl:apply-templates select="ethnic_group"/>
      <xsl:apply-templates select="patient_comments"/>
    </Patient>
  </Patients>
</xsl:template>
```

DICOM TO XML GENERATOR

BACKGROUND OF THE INVENTION

1. Field of the Invention

This invention relates to the field of modeling and data representation, and in particular to the modeling and representation of medical reports, via the use of DICOM SR relational data.

2. Description of Related Art

The Digital Imaging and Communications in Medicine (DICOM) Structured Reporting (SR) standard, and the SR Documentation Model upon which it is based, improves the expressiveness, precision, and comparability of documentation of diagnostic images and waveforms. DICOM SR supports the interchange of expressive compound reports in which the critical features shown by images and waveforms can be denoted unambiguously by the observer, indexed, and retrieved selectively by subsequent reviewers. Findings may be expressed by the observer as text, codes, and numeric measurements, or via location coordinates of specific regions of interest within images or waveforms, or references to comparison images, sound, waveforms, curves, and previous report information. The observational and historical findings recorded by the observer may include any evidence referenced as part of an interpretation procedure. Thus, DICOM SR supports not only the reporting of diagnostic observations, but the capability to document fully the evidence that evoked the observations. This capability provides significant new opportunities for large-scale collection of structured data for clinical research, training, and outcomes assessment as a routine by-product of diagnostic image and waveform interpretation, and facilitates the pooling of structured data for multi-center clinical trials and evaluations.[1]

[1]"Clinical Rationale for the SR Documentation Model and the DICOM Structured Reporting (SR) Standard", Abstract, W. Dean Bidgood, Jr., © 1999.

The DICOM SR is based on a relational data technology, and has been standardized by the National Electrical Manufacturers Association (NEMA). *Supplement 23: Structured Reporting Storage SOP Classes* to the DICOM Standard, published by the DICOM Standards Committee, 1300 N. 17th Street, Rosslyn, Va. 22209 USA, and incorporated by reference herein, introduces the SR Service-Object Pair (SOP) Classes for transmission and storage of documents that describe or refer to any number of images or waveforms or to the specific features that they contain. This standard is expected to be adopted by the medical equipment manufacturers and providers at large to provide text, image, and waveform content in a structured reporting format.

Although the DICOM SR standard provides for a consistent reporting and recording scheme, the use of the information contained in a DICOM SR is limited to DICOM compliant applications that can process this information using the DICOM specific format. Application developers must be DICOM literate, and a methodology for deploying applications that interoperate with other applications outside the DICOM domain has not yet been developed.

In the computer industry, progress has been made in the use of standardized languages and methodologies that facilitate the use of information from a variety of sources by a variety of applications. A standard language that is widely used for processing content material is the World Wide Web Consortium Extensible Markup Language (XML), which is derived from the Standard Generalized Markup Language (SGML), and is designed to describe data and its structure so that it can be easily transferred over a network and consistently processed by the receiver. Because XML is used to describe information as well as structure, it is particularly well suited as a data description language. One of XML's particular strengths is that it allows entire industries, academic disciplines, and professional organizations develop sets of Document Type Definitions (DTDs) and Schemas that can serve to standardize the representation of information within those disciplines. Given a set of DTDs and Schemas, content material that is modeled in conformance with the DTDs and Schemas can be processed by applications that are developed for these DTDs and Schemas.

A further advantage of the use of XML is the wealth of tools that are available for the processing of XML-compatible data. Of particular significance, the "Extensible Stylesheet Language" (XSL) is a language for expressing stylesheets, and the "XSL Transformations" (XSLT) is a language for transforming XML documents into other XML documents, using stylesheets. A stylesheet contains a set of template rules, which are used to match a pattern to a source document, or "source tree" and, when the appropriate match is found, to instantiate a template to a result document, or "result tree". In this manner, XML information that is structured for one application can be relatively easily transformed into a different structure for another application.

BRIEF SUMMARY OF THE INVENTION

Although XML may be considered a relatively new and specialized language, it can be expected that more programmers and other computer professionals will be familiar with XML than those who are familiar with DICOM. Additionally, it can be expected that more general-purpose utilities and applications will be available for use on XML encoded information than will be available for use on DICOM SR encoded information.

An objective of this invention, therefore, is to provide a method and system that facilitate the creation of XML representations of DICOM SR representations and associated information. A further objective of this invention is to provide a method and system that facilitate the creation of XML representations of DICOM SR and other DICOM objects, with minimal information loss. A further objective of this invention is to provide a method and system for creating an XML representation of DICOM objects that is flexible and extensible.

These objectives and others are achieved by providing a conversion system that converts DICOM SR information from a DICOM-formatted file into an XML representation. By providing a mapping between DICOM SR and XML, the DICOM SR content material can be more easily processed by application programs that are DICOM-specific, such as medical analysis programs, as well as by application programs that are not DICOM-specific, such as routine clerical or data-management programs. In a preferred embodiment, a two-phase conversion is employed. The DICOM information is parsed and converted directly into a "raw" XML data set. Thereafter, the "raw" XML is transformed into a proper XML output form, via an XSLT processor. Changes to the desired XML output form can thus be effected via changes in the corresponding XSLT stylesheets.

BRIEF DESCRIPTION OF THE DRAWINGS

The invention is explained in further detail, and by way of example, with reference to the accompanying drawings wherein:

FIGS. 4A-C illustrates example XSLT stylesheets for the conversion of raw XML formatted information into an XML format that is consistent with DICOM-specific DTDs and Schemas.

Throughout the drawings, the same reference numerals indicate similar or corresponding features or functions.

DETAILED DESCRIPTION OF THE INVENTION

As noted above, although applications can be developed that utilize DICOM's relational structured reporting scheme directly, it can be expected that the number of programmers and other computer professions who are familiar with XML and object-oriented technologies and techniques will be substantially greater than those who are familiar with DICOM and relational technologies and techniques.

Copending U.S. patent application "UML MODEL AND XML REPRESENTATIONS OF DIGITAL IMAGING AND COMMUNICATIONS IN MEDICINE STRUCTURED REPORTS (DICOM SR)", Ser. No. 09/686,401, filed Oct. 10, 2000 for Alfredo TiradoRamos, Jingkun Hu, and Yasser alSafadi, Attorney Docket US000268, incorporated by reference herein, discloses a system and method for transforming the DICOM SR specification into a UML (Unified Modeling Language) model to facilitate an understanding of the DICOM SR by non-DICOM systems analysts and system designers. The system and method also includes a transformation of this UML model into XML Document Type Definitions (DTDs) and XML Schemas. The system and method also includes a transformation of a DICOM SR report into a UML document, and further includes a transformation of the UML document into an XML document. Although this system and method is particularly well suited for conveying an understanding of DICOM SR to non-DICOM professionals, and facilitates the development of XML application programs, the transformation of DICOM SR reports to XML via a UML transformation introduces an intermediate level of abstraction. This additional level of model-abstraction may result in a loss of information, because the UML modeling language is primarily designed to model structures and interactions, not data.

Concurrently filed U.S. patent entitled "DICOM XML DTD/SCHEMA GENERATOR", patent number 6,725,231, filed Mar. 27, 2001 for Jingkun Hu and Kwok Pun Lee, Attorney Docket US010070 and incorporated by reference herein, discloses a system and method for transforming the DICOM SR specification directly into XML Document Type Definitions (DTDs) and XML Schemas, and is expected to further increase the use of XML as the language of choice for processing DICOM SRs and other DICOM documents.

This invention is based on the premise that DICOM-related application programs will be developed as XML-enabled applications, and that a variety of existing XML-enabled applications can be used to address clerical and administrative tasks related to the information contained in the DICOM reports.

Figure 1:
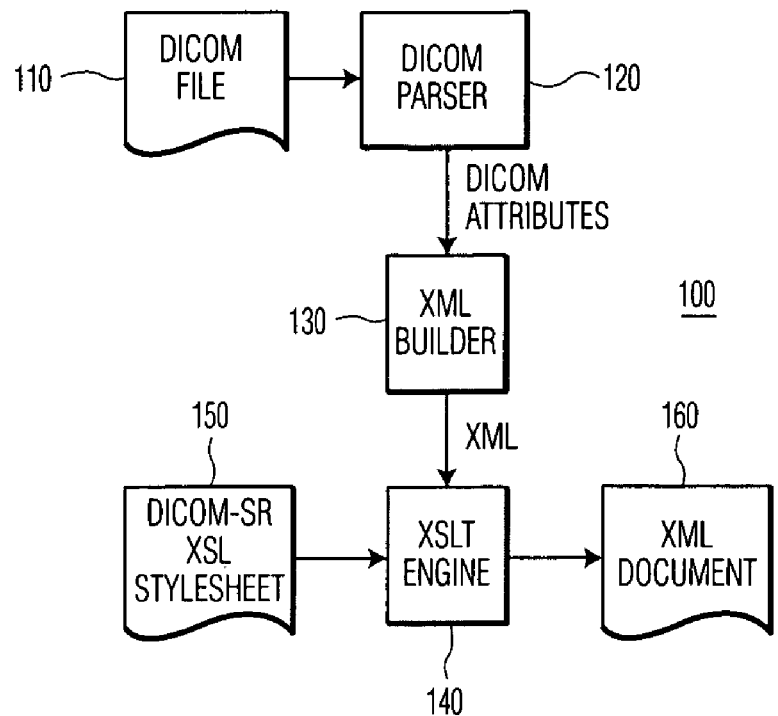
FIG. 1 illustrates an example block diagram of a DICOM to XML conversion system in accordance with this invention.

FIG. 1 illustrates an example block diagram of a DICOM to XML conversion system 100 in accordance with this invention. The conversion system 100 transforms a DICOM input file 110, such as a DICOM Structured Report (DICOM-SR) into a corresponding XML document 160. A DICOM parser 120 extracts the attributes from the DICOM input file 110, and provides these attributes to an XML builder 130. In the DICOM environment, an attribute is the core data conveyance device. Attributes in a diagnostic report, for example, will identify the patient, the diagnostician, the procedure used, the particular results found, references to other items, such as Xray images, coordinates of items of interest in the reference image, and so on.

In a preferred embodiment, the XML builder 130 is configured to effect a straightforward translation of each DICOM attribute, without consideration for the particular format or structure required by an application program that is intended to process the DICOM-XML attributes. Alternatively, the XML builder 130 may be configured to format the DICOM-XML attributes in accordance with a particular set of XML DTDs and Schemas that are designed for use in a particular application. By partitioning the XML-conversion from the XML-formatting, the resultant system is expected to be more flexible and robust than a composite system, consistent with the principles of well structured designs. For ease of reference, the directly-translated attributes from the XML builder 130 are herein referred to as "raw" XML data.

In a preferred embodiment, the raw XML data is processed via an XSLT (Extensible Stylesheet Language Transformation) engine 140. The additional advantage of segregating the XML-conversion from the XML-formatting is that existing XML-transformation tools and techniques can be used to effect the desired output XML format structure. In this preferred use of XSLT, the desired output XML format is specified using XSLT stylesheets 150, discussed further below. These stylesheets 150 are defined based on DTDs and Schemas that define the format used by an application program. If a DICOM-XML standard is adopted for DICOM processing applications, then the use of stylesheets 150 that are compatible with this standard will allow the DICOM-XML data that is produced by the conversion system 100 to be processed by each application that is compatible with the standard. If a variety of DICOM-XML formats are defined, a different set of stylesheets 150 can be provided for each format, and thereby allowing the use of the same builder 130, regardless of the particular output format.

Figure 2:
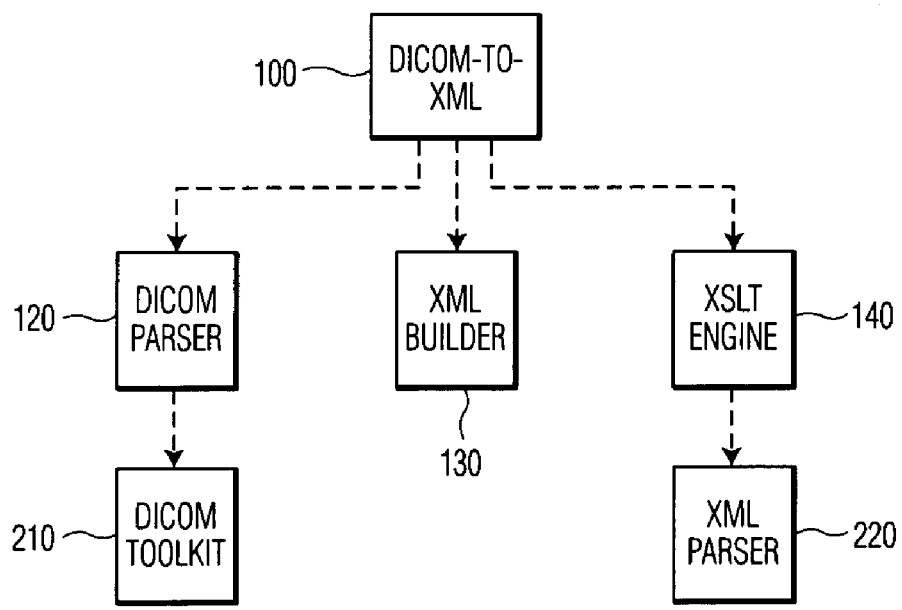
FIG. 2 illustrates an example component structure diagram of a DICOM to XML conversion system in accordance with this invention.

FIG. 2 illustrates an example component structure diagram of a DICOM to XML conversion system 100 in accordance with this invention. As illustrated, the DICOM-to-XML converter 100 calls each of the three processes 120, 130, 140, as required. In a preferred embodiment, the DICOM parser 120 accesses any of a variety of conventional DICOM "toolkits" that are available commercially, thereby alleviating the development tasks for routine DICOM-related processing tasks. For example, the DICOM file 110 in FIG. 1 is typically a "binary" file having a well-defined encoding scheme. A DICOM toolkit 210 will include the utility programs, subprograms, and function calls that facilitate the decoding of this binary data into a more convenient form for processing by the parser 120.

After the DICOM attributes are decoded from the DICOM file 110 by the DICOM parser 120, the DICOM-to-XML converter 100 invokes the XML builder 130 to create XML data corresponding to each of the parsed DICOM attributes.

Figure 3:
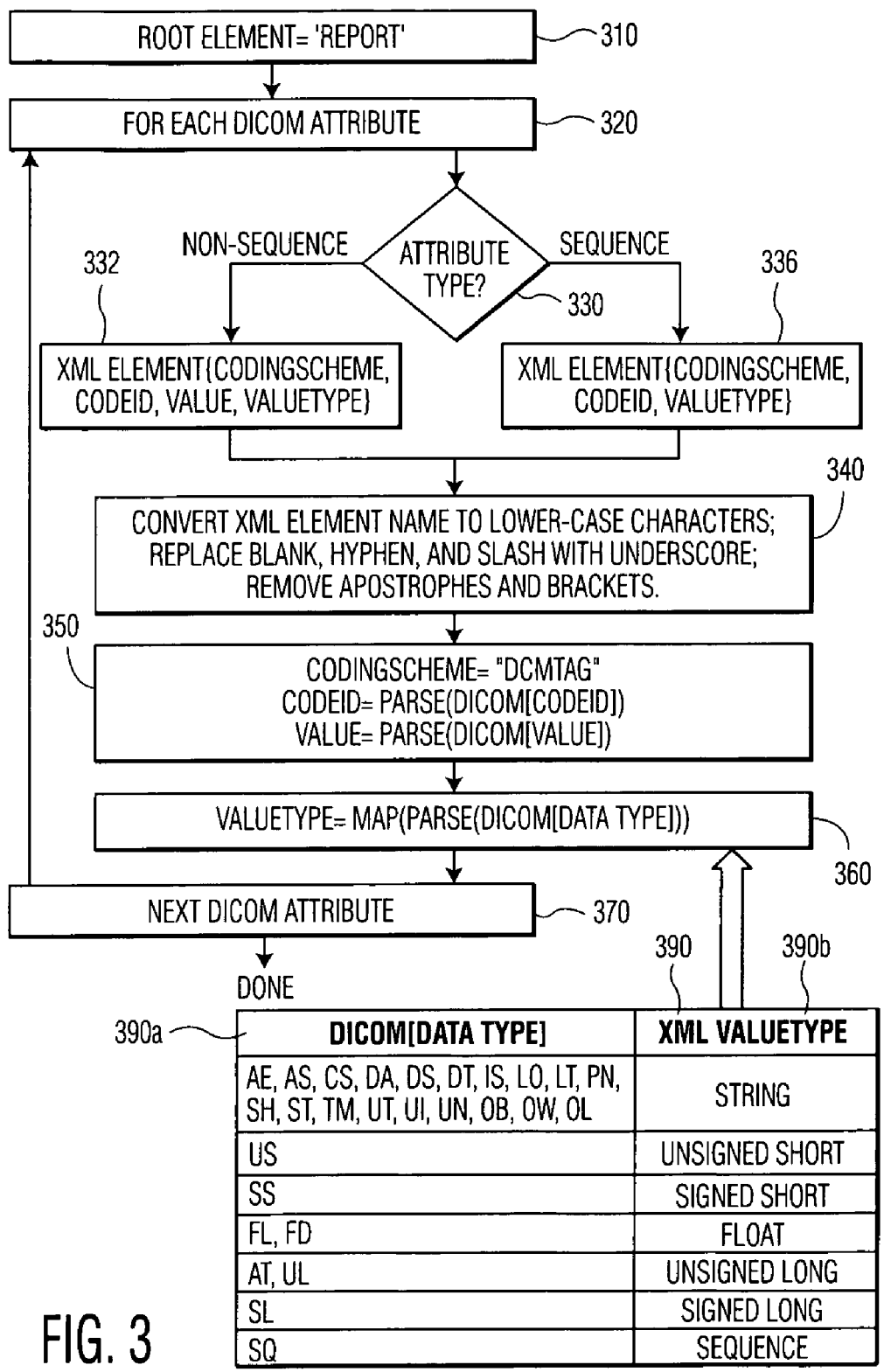
FIG. 3 illustrates an example flow diagram for the conversion of a DICOM object into an XML representation in accordance with this invention.

FIG. 3 illustrates an example flow diagram for the conversion of a DICOM object into an XML representation in accordance with this invention. The XML data is identified by a root element, at 310; in this example, the root element for the XML data is defined to be "report". Each DICOM attribute is subsequently processed, via the loop 320-370. If a DICOM attribute includes other attributes, each of the other attributes are processed recursively within the loop 320-370.

If, at 330, the DICOM attribute is a "sequence" ("SQ" in DICOM terminology), an XML element is created, at 336, having XML attributes of "CodingScheme", "CodeID", and "ValueType", discussed further below. If, at 330, the DICOM attribute is not a sequence, an XML element is created, at 332, having XML attributes of "CodingScheme", "CodeID", "Value", and "ValueType". The name of the XML element is derived by converting the DICOM attribute name, using the rules illustrated at block 340. Upper-case letters are converted to lower-case; each blank, hyphen, and slash is replaced with an underscore; and each apostrophe and bracket is deleted.

The XML attributes are defined as illustrated at block 350. All elements have a common CodingScheme value, such as "DCMTAG". The DICOM codeID, which was parsed in the DICOM parser 120 of FIG. 2, is used as the value of the XML CodeID attribute, and, if the element is not a sequence element, the Value attribute is given the DICOM attribute value, which was also parsed in the DICOM parser 120.

The mapping of DICOM attribute data types 390a to the XML ValueType attributes 390b is illustrated at 390. DICOM attributes of SS and US type are assigned ValueType "signed short" and "unsigned short", respectively; attributes of FL and FD type are assigned ValueType "float"; attributes of AT, and UL type are assigned Value Type "unsigned long"; attributes of SL type are assigned Value Type "signed long"; and attributes of type SQ are assigned ValueType "sequence". All other attribute types are assigned ValueType "string". This mapping is effected at block 360, based on the parsed value of the DICOM attribute's data type.

After conversion of each DICOM attribute to a corresponding XML element, the DICOM-to-XML converter 100 invokes the XSLT engine 140, which may be any of a variety of commonly available XSLT engines, to provide the desired XML output format, as discussed above. The XSLT engine uses a conventional XML parser 220 to facilitate the identification of each data item in the raw XML data for subsequent output formatting based on the aforementioned stylesheets 150 of FIG. 1.

Figure 4C:
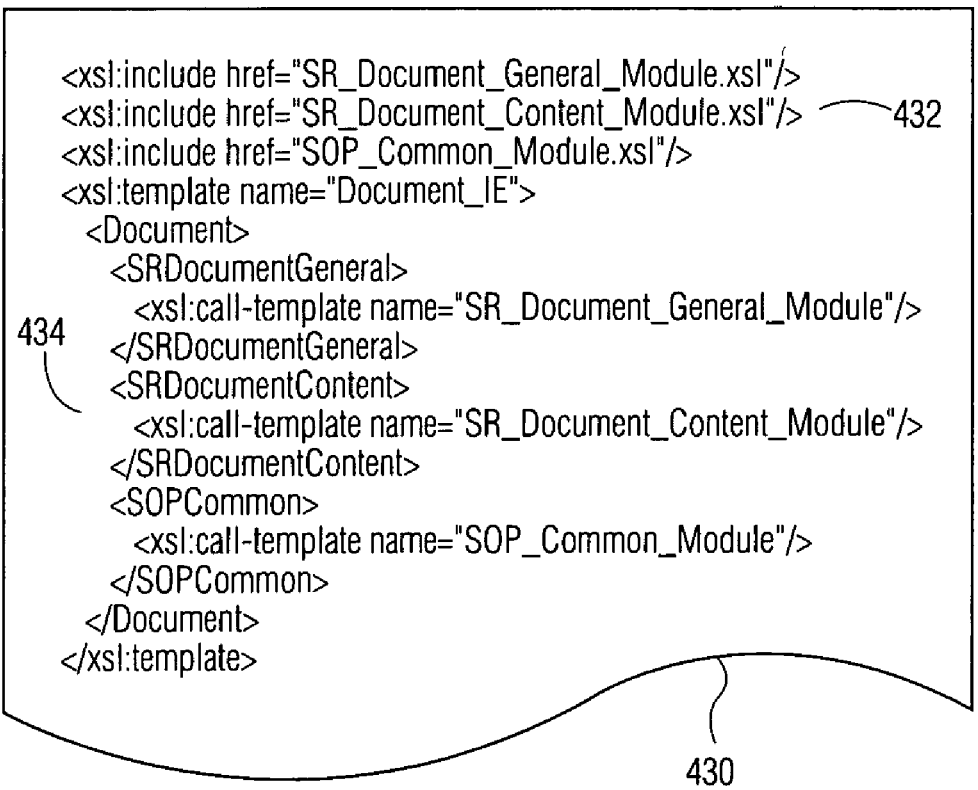

FIGS. 4A-C illustrates example XSLT stylesheets for the conversion of raw XML formatted information into an XML format that is consistent with DICOM-specific DTDs and Schemas. As noted above, these DTDs and Schemas will have been defined for use by applications designed to process DICOM-related material, and particularly DICOM Structured Reports (SRs).

FIG. 4A corresponds to the DICOM-SR XSLT high-level structure stylesheet 410. As illustrated in the "include" portion 412 of the stylesheet 410, the high-level structure includes references ("href=") to five different stylesheets, "Patient_IE.xsl", "Study_IE.xsl", "Series_IE.xsl", "Equipment_IE.xsl", and "Document_IE.xsl", corresponding to the five "Information Entities" (IEs) in the DICOM SR. At 414, the stylesheet 410 calls for a match between the root element in the raw XML file and the word "report", which was assigned to the root element of the raw XML file at 310 in FIG. 3. Upon finding the match, the stylesheet 410 provides, at portion 416, header information for the XML file, SRDocument, that is being created, including the report identification, and the report date. At portion 418, each of the Patient, Study, Series, Equipment, and Document templates/stylesheets are called to produce the remainder of the SRDocument.

FIG. 4B corresponds to the aforementioned "Patient_IE.xsl" stylesheet 420 that is referenced in the high-level structure stylesheet 410. Each element within the DICOM "Patient" IE has a corresponding template for outputting the contents of the element in a particular form. For example, the template for placing the patient's name into the XML output file is illustrated in FIG. 4B as "patients_name_template" 422; the template for placing the patient's identification and birthdate are illustrated, as "patients_id_template" 424 and "patients_birth_date_template" 426, and so on. As noted above, by using an XSLT engine to create the appropriately formatted output based on stylesheets that contain templates for creating the output, different output formats can be provided by merely changing the appropriate templates. The "Study_IE.xsl", "Series_IE.xsl", and "Equipment_IE.xsl" stylesheets are similarly encoded, using the appropriate calls to templates corresponding to elements within each of these Information Entities.

FIG. 4C corresponds to the remaining "Document_IE.xsl" stylesheet 430. In a preferred embodiment the "Document_IE.xsl" is partitioned into three simpler stylesheets: "SR_Document_General_Module.xsl", "SR_Document_Content_Module.xsl", and "SOP_Common.xsl", corresponding to the DICOM SR Document General, SR Document Content, and SOP Common modules of the DICOM Document Information Entity. These module stylesheets are included in the stylesheet 430, at 432, and each of the templates are invoked to provide the appropriately formatted XML output corresponding to the DICOM Document IE, at 434. The DICOM SR includes three forms of Information Object Definitions (IODs): a basic text SR, an enhanced SR, and a comprehensive SR. Each of these forms of IODs is provided by providing separate "SR_Document_Content_Module.xsl" stylesheets.

The foregoing merely illustrates the principles of the invention. It will thus be appreciated that those skilled in the art will be able to devise various arrangements which, although not explicitly described or shown herein, embody the principles of the invention and are thus within the spirit and scope of the following claims.

We claim:

1. A method for mapping a DICOM-SR document into an XML document, comprising:
    mapping each DICOM attribute of a plurality of DICOM attributes in the DICOM-SR document into a corresponding XML element of a plurality of XML lements,
    outputting each XML element of the plurality of XML elements to the XML document, in a format that conforms to an XML document-type-definition of the XML document, and
    parsing each DICOM attribute to segregate a DICOM data type, and a DICOM codeID from the DICOM attribute,
    wherein the mapping includes:
        assigning the DICOM codeID to a first attribute of the corresponding XML element,
        mapping the DICOM data type to a corresponding value type of the corresponding XML element, and
        assigning the corresponding value type to a second attribute of the corresponding XML element, and wherein the mapping of each DICOM attribute into a corresponding XML element is independent of the XML document-type-definition of the XML document.

2. The method of claim 1, wherein outputting each XML element includes formatting the XML element via one or more XSLT templates to conform to the XML document-type-definition.

3. The method of claim 2, wherein the formatting of the XML element is via an XSLT engine.

4. The method of claim 2, wherein the one or more XSLT templates correspond to one or more DICOM Information Entities.

5. The method of claim 1, further including parsing the DICOM attribute to segregate a DICOM attribute value, and wherein the mapping further includes assigning the DICOM attribute value to a third attribute of the corresponding XML element.

6. A computer-implemented DICOM to XML conversion system, comprising:
a memory storing:
a DICOM parser that is configured to provide a plurality of DICOM attributes from a DICOM data file,
an XML formatter, operably coupled to the DICOM parser, that is configured to provide a plurality of XML elements corresponding to the plurality of DICOM attributes, and
an XML builder operably coupled between the DICOM parser and the XML formatter, said XML builder being configured to effect a direct mapping of each DICOM attribute of the plurality of DICOM attributes into a corresponding XML element of the plurality of XML elements independent of an XML document-type-definition of an XML document comprising the plurality of XML elements, wherein the DICOM parser is configured to parse each DICOM attribute to provide a DICOM data type, and a DICOM codeID from the DICOM attribute, and the XML builder is configured to:
assigning the DICOM codeID to a first attribute of the corresponding XML element;
mapping the DICOM data type to a corresponding value type of the corresponding XML element; and
assigning the corresponding value type to a second attribute of the corresponding XML element.

7. The DICOM to XML conversion system of claim 6, wherein the XML formatter is configured to provide the plurality of XML elements in a format that conforms to the XML document-type-definition of the XML document.

8. The DICOM to XML conversion system of claim 7, wherein the XML formatter includes an XSLT engine that is configured to provide the plurality of XML elements based on one or more XSLT stylesheet templates that conform to the XML document-type-definition.

9. The DICOM to XML conversion system of claim 8, wherein the one or more XSLT stylesheet templates correspond to one or more DICOM Information Entities.

10. The DICOM to XML conversion system of claim 6, wherein the DICOM parser is further configured to parse each DICOM attribute to provide a DICOM attribute value, and the XML builder is further configured to assign the DICOM attribute value to a third attribute of the corresponding XML element.

* * * * *